United States Patent
Ou

(10) Patent No.: US 9,457,292 B2
(45) Date of Patent: Oct. 4, 2016

(54) PARAXYLENE PRODUCTION PROCESS AND APPARATUS

(71) Applicant: ExxonMobil Chemical Patents Inc., Baytown, TX (US)

(72) Inventor: John Di-Yi Ou, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 510 days.

(21) Appl. No.: 14/035,660

(22) Filed: Sep. 24, 2013

(65) Prior Publication Data

US 2014/0023563 A1 Jan. 23, 2014

Related U.S. Application Data

(62) Division of application No. 13/108,410, filed on May 16, 2011, now Pat. No. 8,569,559.

(60) Provisional application No. 61/358,713, filed on Jun. 25, 2010.

(30) Foreign Application Priority Data

Oct. 1, 2010 (EP) .................................... 10185223

(51) Int. Cl.
| | |
|---|---|
| *B01D 3/00* | (2006.01) |
| *C07C 5/27* | (2006.01) |
| *C07C 7/12* | (2006.01) |
| *C07C 7/14* | (2006.01) |
| *C07C 7/04* | (2006.01) |
| *C07C 7/144* | (2006.01) |
| *B01J 29/40* | (2006.01) |
| *B01J 35/02* | (2006.01) |
| *B01J 35/10* | (2006.01) |

(52) U.S. Cl.
CPC ............. *B01D 3/009* (2013.01); *C07C 5/2737* (2013.01); *C07C 7/04* (2013.01); *C07C 7/12* (2013.01); *C07C 7/14* (2013.01); *C07C 7/144* (2013.01); *B01J 29/40* (2013.01); *B01J 35/023* (2013.01); *B01J 35/1014* (2013.01); *B01J 2219/00006* (2013.01); *C07C 2529/40* (2013.01); *Y02P 20/52* (2015.11)

(58) Field of Classification Search
CPC .............................. C07C 5/2737; B01J 8/001
See application file for complete search history.

(56) References Cited

U.S. PATENT DOCUMENTS

| | | | |
|---|---|---|---|
| 3,856,871 A * | 12/1974 | Haag ........................ | B01J 29/40 585/473 |
| 6,689,929 B2 | 2/2004 | Williams et al. | |
| 6,878,855 B2 | 4/2005 | Deckman et al. | |
| 7,439,412 B2 | 10/2008 | Ou et al. | |
| 7,626,065 B2 | 12/2009 | Ou et al. | |
| 2010/0152508 A1 | 6/2010 | Ou et al. | |
| 2011/0263918 A1* | 10/2011 | Ou ........................... | B01J 29/40 585/481 |

FOREIGN PATENT DOCUMENTS

| | | |
|---|---|---|
| WO | WO 2005/075389 | 8/2005 |
| WO | WO 2005/075390 | 8/2005 |

* cited by examiner

*Primary Examiner* — Lessanework Seifu

(57) ABSTRACT

The invention concerns a process for the production of paraxylene and an apparatus suitable for said process. The process separates the overhead from a xylenes re-run into a xylene-rich stream and a xylene-lean stream. The xylene-lean stream is isomerized under conditions such that the xylenes are in the liquid phase.

4 Claims, 3 Drawing Sheets

PARAXYLENE PRODUCTION PROCESS AND APPARATUS

CROSS REFERENCE TO RELATED APPLICATION

This application is a Divisional Application of U.S. Ser. No. 13/108,410, filed May 16, 2011, now allowed, and claims the benefit of Provisional Application No. 61/358,713, filed Jun. 25, 2010, the disclosures of which is incorporated by reference in their entirety.

FIELD OF THE INVENTION

The invention relates to a process for producing xylenes and more particularly a process for producing paraxylene (PX).

BACKGROUND OF THE INVENTION

An equilibrium mixture of xylenes contains roughly 24% para-xylene (PX), 56% meta-xylene (MX), and 20% ortho-xylene (OX). PX is relatively high value as compared with MX and OX, and it is desirable to isomerize OX and/or MX to PX. Vapor phase and liquid phase processes for isomerizing PX-lean streams to equilibrium for subsequent PX is recovery are described in numerous patents. It is an active area of research.

A typical paraxylene production process involves the so-called xylene loop. An example is illustrated in FIG. 1, which is a simplified flow diagram showing three major operations that occur in the xylene loop. There are many vaporization and condensation steps.

Liquid feed, typically a C8+ aromatic feedstream which has previously been processed by known methods to remove C7-species (particularly benzene and toluene), is fed by conduit 1 to xylenes re-run 3, an apparatus per se well known in the art. The xylenes re-run (or more simply a fractionation column) vaporizes the feed and separates the C8 aromatics into an overhead mixture 5 of xylenes (OX, MX, and PX) and ethylbenzene (EB), and a bottom product 61 comprising C9+ aromatics. The overhead mixture typically has a composition of about 40-50% metaxylene (MX), 15-25% PX, 15-25% OX, and 10-20% EB. Unless otherwise noted herein, percentages are % weight. The overhead is then condensed in condenser 7, an apparatus also per se well-known in the art, and becomes the feed for the PX recovery unit 15, via conduit 9 and 13, a portion of the condensed overhead may be returned to re-run 3 as reflux via conduits 9 and 11.

The PX recovery unit 15 may employ crystallization technology, adsorption technology, or extraction technology, each per se well known in the art. These technologies separate PX from its isomers and are capable of producing high purity PX up to 99.9%, which is taken from unit 15 via conduit 17. Shown in FIG. 1 is the case where unit 15 is an adsorptive separation unit, such as a Parex™ Unit, in which case typically the extract 17, which comprises a desorbent, such as PDEB (paradiethylbenzene), needs to be separated, such as by distillation, from the desired extract PX in distillation column 19, which generates an overhead 23 that is condensed in condenser 25 to yield a liquid stream 27, which is a high purity PX stream. This stream 27 may be taken off via conduit 31 and optionally a portion may be returned to column 19 as reflux via conduit 29. The desorbent is returned to the PX recovery system 15 via conduit 21. Raffinate from the recovery system 15, comprising MX, OX, EB, and some PX, is removed via conduit 65 and sent to unit 37, discussed below. Note: a portion of raffinate in 65 may be recovered and marketed as low-value solvent xylene.

The raffinate 65, which comprises mainly MX, OX, EB, and desorbent is sent to fractionation column 37, generating overhead 33 and bottoms 63. Overhead 33 contains MX and OX, which is condensed in condenser 32 and sent via conduit 35 and then 41 to isomerization unit 43, discussed in more detail below. A portion may be returned to is fractionator 37 via conduit 35 and then 39 as reflux. The desorbent in the bottoms product is returned to 15.

A stream consisting essentially of MX and OX and EB is sent to isomerization unit 43, an apparatus per se known in the art, to isomerize the MX and OX and optionally EB to PX. Conventionally unit 43 is a vapor phase isomerization unit. Conventionally there are one or more heat exchangers or furnaces associated with the system shown in FIG. 1 between the PX recovery unit 15 and the isomerization unit that are not shown for convenience of view. Likewise, hydrogen separators and hydrogen compressors are also not shown for convenience of view. These and other features, such as valves and the like, would be apparent to one of ordinary skill in the art in possession of the present invention.

The product of the isomerization unit 43 is sent via conduit 51 to the C7-distillation tower 53, which separates the product of isomerization into a bottom stream 59 comprising equilibrium xylenes and the overhead 47, comprising C7-aromatics, e.g., benzene and toluene. The overhead product is condensed in condenser 45 and then the distribution of liquid product via conduit 49 may be apportioned as desired between conduit 57 and conduit 55, the former of which may be disposed of in numerous ways which would be well-known per se in the art, and the latter conduit returning C7-aromatics as reflux to tower 53. The bottoms product 59 of distillation tower 53 is then sent to xylenes re-run 3, either merging with feed 1 as shown in the figure, or it may be introduced by a separate inlet (not shown).

Note that as used herein the term "raffinate" is used to mean the portion recovered from the PX recovery unit 15, whether the technology used is adsorptive separation, crystallization, or membrane, and then is sent to the isomerization unit 43, conventionally a vapor phase isomerization unit, which uses technology also per se well-known. The xylene isomerization unit (whether vapor phase or liquid phase) accomplishes two major things. It isomerizes the lower valued MX and OX to higher value PX and it also turns EB into benzene/toluene and light gases (so-called "EB destruction") or optionally, isomerize EB to xylenes. EB destruction or EB isomerization prevents the build up of EB within the xylenes loop. Products from the isomerization unit are distilled to separate C7-compounds (particularly toluene and benzene) prior to being recycled back to the xylene re-run.

Particularly relevant patents include U.S. Pat. No. 6,689,929 U.S. Pat. No. 6,878,855; WO 2005/075389; and WO 2005/075390.

Recently the present inventor, along with others, has described with particularity processes involving the use, at least partially, of liquid phase isomerization in U.S. Provisional Application Ser. Nos. 12/612,007 and 61/326,445.

The present inventor has now discovered a process for PX production which in embodiments provides for a significant reduction in energy consumption by eliminating excessive vaporization and unnecessary recycling.

SUMMARY OF THE INVENTION

The invention is directed to a paraxylenes production process, wherein the overhead stream from a xylenes rerun is sent to a PX separation unit to produce a PX-rich stream and a PX-lean stream. The PX-rich stream is sent to a PX recovery unit and the PX-lean stream is sent to a liquid isomerization unit.

In an embodiment, the PX separation unit separates PX from MX, OX, and EB or optionally, PX and EB from MX and OX, by adsorption, crystallization, or membrane technology.

In a preferred embodiment the separation of PX from its isomers OX and MX using pressure swing adsorption (PSA).

It is an object of the invention to provide a process for the production of paraxylene including a PX separation step and a liquid phase isomerization process which, compared to conventional xylenes production processes, provides at least one of the advantages selected from low investment, low energy costs, avoidance of numerous condensation and/or distillation steps, and higher paraxylene purity.

These and other objects, features, and advantages will become apparent as reference is made to the following detailed description, preferred embodiments, examples, drawings, and appended claims.

BRIEF DESCRIPTION OF THE DRAWINGS

In the accompanying drawings, like reference numerals are used to denote like parts throughout the several views.

DETAILED DESCRIPTION

Figure 1:
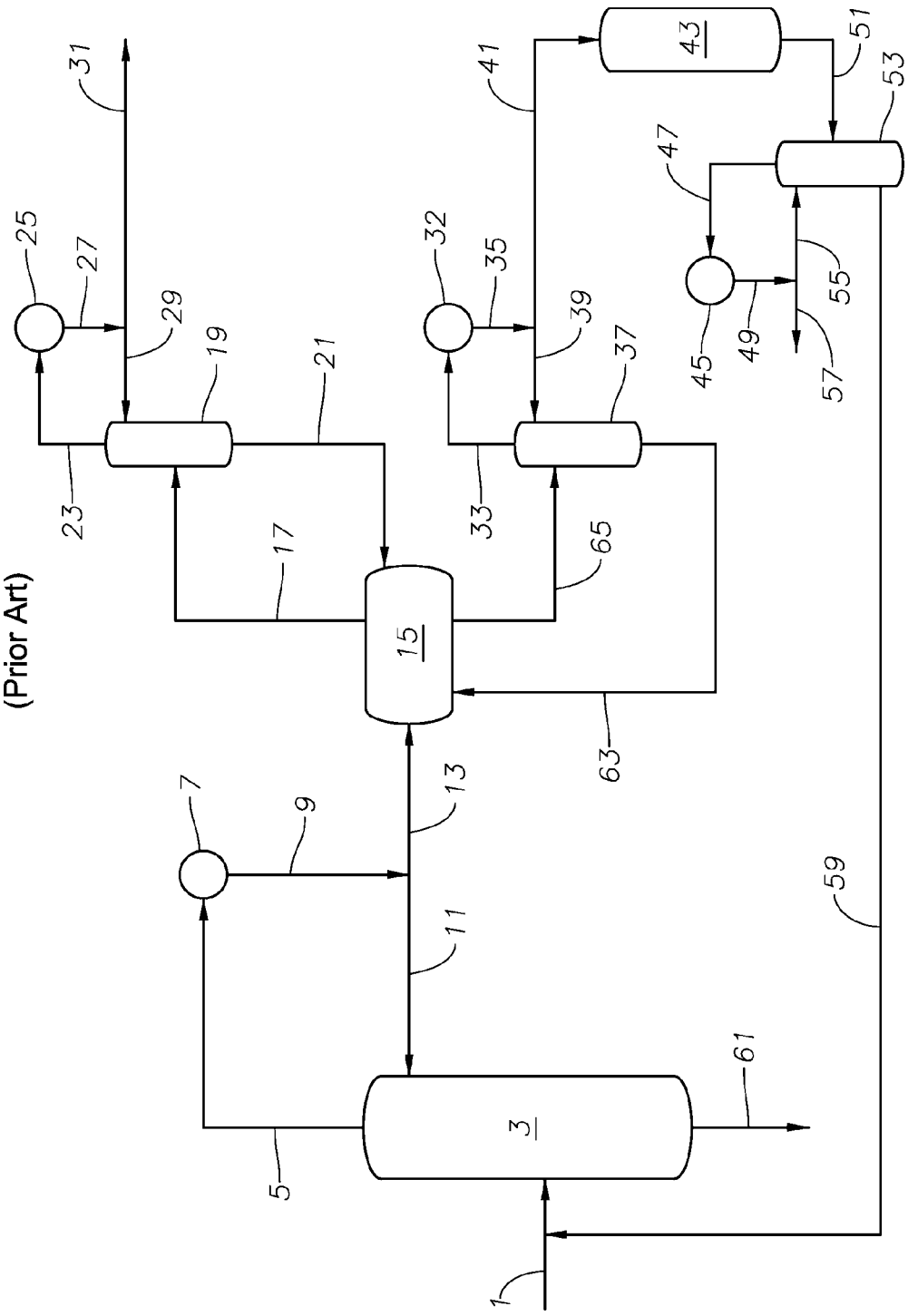
FIG. 1 is a schematic diagram illustrating a prior art PX production process.

According to the invention, there is provided a process for production of paraxylene including paraxylene recovery and the liquid phase isomerization of PX-lean xylenes at a temperature and a pressure sufficient to maintain the xylenes in liquid phase. A preferred temperature is less than 295° C.

In an embodiment, there is a process for the production of paraxylene including separation of xylenes from C9+ aromatics in a column to generate a xylenes-rich overhead, followed by separation of PX from OX and MX, the improvement comprising an intermediate step including separation of said xylene-rich overhead into a PX-rich stream and a PX-lean stream, and sending the latter stream to a liquid isomerization unit, returning all or a portion of the product of said liquid isomerization unit to said column.

In embodiments the process utilizes crystallization technology and/or an adsorptive separation process, such as the Parex™ Process, and/or a membrane process, for PX recovery.

In embodiments the process utilizes a catalyst for liquid isomerization comprising a zeolite, preferably at least one selected from the group consisting of ZSM-5 and MCM-49. Recently such a process has been described more fully in U.S. Provisional Application Ser. No. 61/326,445.

In embodiments the liquid isomerization process utilizes a catalyst comprising ZSM-5 along with a binder or the ZSM-5 may be self-bound.

In preferred embodiments the catalyst is characterized by one or more of the following characteristics:

the ZSM-5 is in the proton form (HZSM-5);
the ZSM-5 has a crystal size of less than 0.1 microns;
the ZSM-5 has a mesoporous surface area (MSA) greater than 45 m²/g;

the ZSM-5 has a zeolite surface area (ZSA) to mesoporous surface area (MSA) ratio of less than 9;
a silica to alumina weight ratio in the range of 20 to 50.

The catalyst can be formulated using various techniques such as extrusion, pelletization, oil dropping, spray drying, and the like, techniques which are per se well-known in the art. Optionally, binder materials such as alumina, silica, clay, aluminosilicate, may be used in the formulation. In preferred embodiments, the catalyst is characterized by one or more of the following properties with respect to the binder:

the zeolite:binder weight ratio is from 1:9 to 9:1;
the binder preferably comprises silica, alumina, and aluminosilicate;
the catalyst is preferably extruded using acetic acid as extrusion aid.

The preferred reactor is fixed bed and the flow may be up or down.

In embodiments the process can be operated in a continuous mode with ppm levels of $H_2$ dissolved in the feed and in other embodiments in a cyclic mode without the $H_2$ in feed but with periodic regenerations.

The isomerization step comprises contacting a feedstream comprising C8 aromatic hydrocarbons with a catalyst suitable for isomerization, at a temperature and pressure sufficient to keep the reactant in liquid phase, preferably at a temperature below 295° C., preferably below 280° C. The flow rate can be selected by one of ordinary skill in the art in possession of the present disclosure, but may advantageously be selected within the range from 1 to 100 WHSV, preferably from 1 to 20 WHSV, and more preferably from 1 to 10 WHSV.

As previously mentioned, liquid phase isomerization per se is well-known and reference may be made to U.S. Pat. Nos. 6,180,550; 6,448,459; 6,827,866; 7,244,409; 7,371,913; 7,495,137; 7,592,499; U.S. patent application No. 2009-0182182; and U.S. Ser. No. 12/612,007. Details of liquid and vapor-phase separation of PX from its isomers OX and MX is also per se well-known, and details may be found in patents too numerous to mention. More generally reference may be made to Handbook of Petroleum Refining Processes, Third Edition, McGraw-Hill Handbooks, Robert A. Meyers, Editor (2004).

A fuller appreciation of the present invention may be obtained by reference to FIGS. 2 and 3 which are described below in the context of specific examples. The figures and examples should not be taken as limiting but rather one of skill in the art will understand that numerous variations are possible within the scope of the appended claims.

Figure 2:
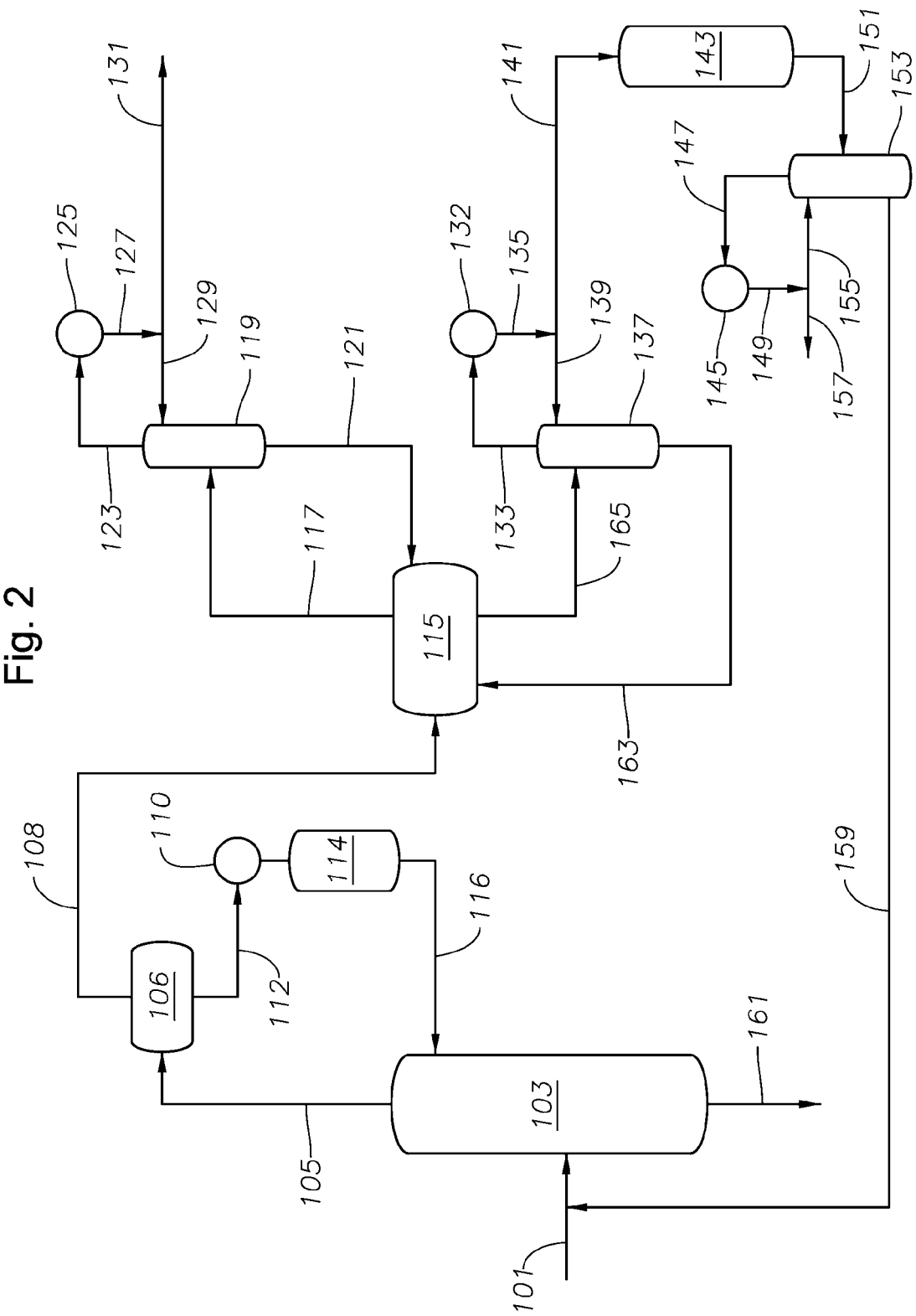
FIGS. 2 and 3 are schematic diagrams illustrating embodiments of the present invention, incorporating liquid isomerization in a PX production process.

As shown in FIG. 2, the problems of excessive vaporization/condensation and recycle can be mitigated by placing a vapor-phase PX separation unit 106 to separate the overhead stream 105 from the xylenes re-run 103 into a PX-rich stream 108 and a PX-lean stream 112. Similar to FIG. 1, re-run 103 is provided a feedstream 101 comprising xylenes (optionally merged with recycle from the system, e.g., a stream provided by conduit 159, as explained further herein). The vapor-phase PX separator 106 may be an adsorption unit, a membrane unit, or any other technology capable of separating PX from EB, MX and OX or is PX/EB from MX and OX in a vapor phase operation. In the preferred case 106 is a pressure swing adsorption unit (PSA) per se well-known in the art. The PX-rich stream will be condensed and fed to a PX recovery unit (preferably an adsorptive separation unit) 115, discussed in more detail below, such as a PAREX™ unit, crystallization unit or membrane separation unit for PX recovery. The PX-lean stream 112, which contains mostly MX and OX and optionally EB, will be condensed in condenser 110 and isomerized in liquid phase isomerization unit 114 to raise the PX concentration. The product from the liquid isomerization is sent back to the xylenes re-run as a reflux via conduit 116.

The overheads 108 is sent to the PX recovery unit 115, which may employ crystallization technology, adsorption technology, or extraction technology, each per se well known in the art. These technologies separate PX from its isomers and are capable of producing high purity PX up to 99.9%, which is taken from unit 115 via conduit 117. Shown in FIG. 2 is the case where unit 115 is an adsorptive separation unit, such as a Parex™ Unit, in which case typically the extract 117, which comprises a desorbent, such as PDEB (paradiethylbenzene), needs to be separated, such as by distillation, from the desired extract PX in distillation column 119, which generates an overhead 123 that is condensed in condenser 125 to yield a liquid stream 127, which is a high purity PX stream. This stream 127 may be taken off via conduit 131 and optionally a portion may be returned to column 119 as reflux via conduit 129. The desorbent is returned to the PX recovery system 115 via conduit 121. Raffinate from the recovery system 115, comprising MX, OX, EB, and some PX, is removed via conduit 165 and sent to unit 137, discussed below. Again, raffinate such as in conduit 165 is often taken off (valve and/or lines not shown) and marketed as low-value solvent xylene.

The raffinate 165, which comprises mainly MX, OX, EB, and desorbent is sent to fractionation column 137, generating overhead 133 and bottoms 163. Overhead 133 contains MX and OX, which is condensed in condenser 132 and sent via conduit 135 and then 141 to isomerization unit 143, discussed in more detail below. A portion may be returned to fractionator 137 via conduit 135 and then 139 as reflux. The desorbent in the bottoms product is returned to the unit designated 115.

A stream consisting essentially of MX and OX and EB is sent to isomerization unit 143, an apparatus per se known in the art, to isomerize the MX and OX and optionally EB to PX. Conventionally unit 143 is a vapor phase isomerization unit. Conventionally there are one or more heat exchangers or furnaces associated with the system shown in FIG. 2 between the PX recovery unit 115 and the isomerization unit that are not shown for convenience of view. Likewise, hydrogen separators and hydrogen compressors are also not shown for convenience of view. These and other features, such as valves and the like, would be apparent to one of ordinary skill in the art in possession of the present invention.

The product of the isomerization unit 143 is sent via conduit 151 to the C7-distillation tower 153, which separates the product of isomerization into a bottom stream 159 comprising equilibrium xylenes and the overhead 147, comprising C7-aromatics, e.g., benzene and toluene. The overhead product is condensed in condenser 145 and then the distribution of liquid product via conduit 149 may be apportioned as desired between conduit 157 and conduit 155, the former of which may be disposed of in numerous ways which would be well-known per se in the art, and the latter conduit returning C7-aromatics as reflux to tower 153. The bottoms product 159 of distillation tower 153 is then sent to xylenes re-run 103, either merging with feed 101 as shown in the figure, or it may be introduced by a separate inlet (not shown).

Compared to the conventional process shown in FIG. 1, the new process reduces significantly the amount of MX and OX circulating in the loop. It also takes advantages of the existing vapor stream in the xylenes re-run overhead 105 and the liquid stream 116 from the xylenes re-run condensor 110. These features in particular contribute to the reduction of energy consumption.

Alternatively, a liquid-phase PX separator could be used for unit 106 (in conjunction with a condenser, not shown) to separate the liquid stream from the re-run condensor into a liquid PX-rich and a liquid PX-lean streams. The liquid-phase PX separator could be an adsorption unit, a membrane unit, crystallization unit, or any other technology capable of separating PX from EB, MX and OX or PX/EB from MX and OX in a liquid phase operation. The PX-rich stream will be fed to an adsorptive separation unit such as a PAREX™ unit for PX recovery. The PX-lean stream, which contains mostly MX and OX, will be isomerized in liquid phase to raise the PX concentration. The product from the liquid isomerization is sent back to the re-run as a reflux. A similar benefit of energy saving could be realized.

Figure 3:
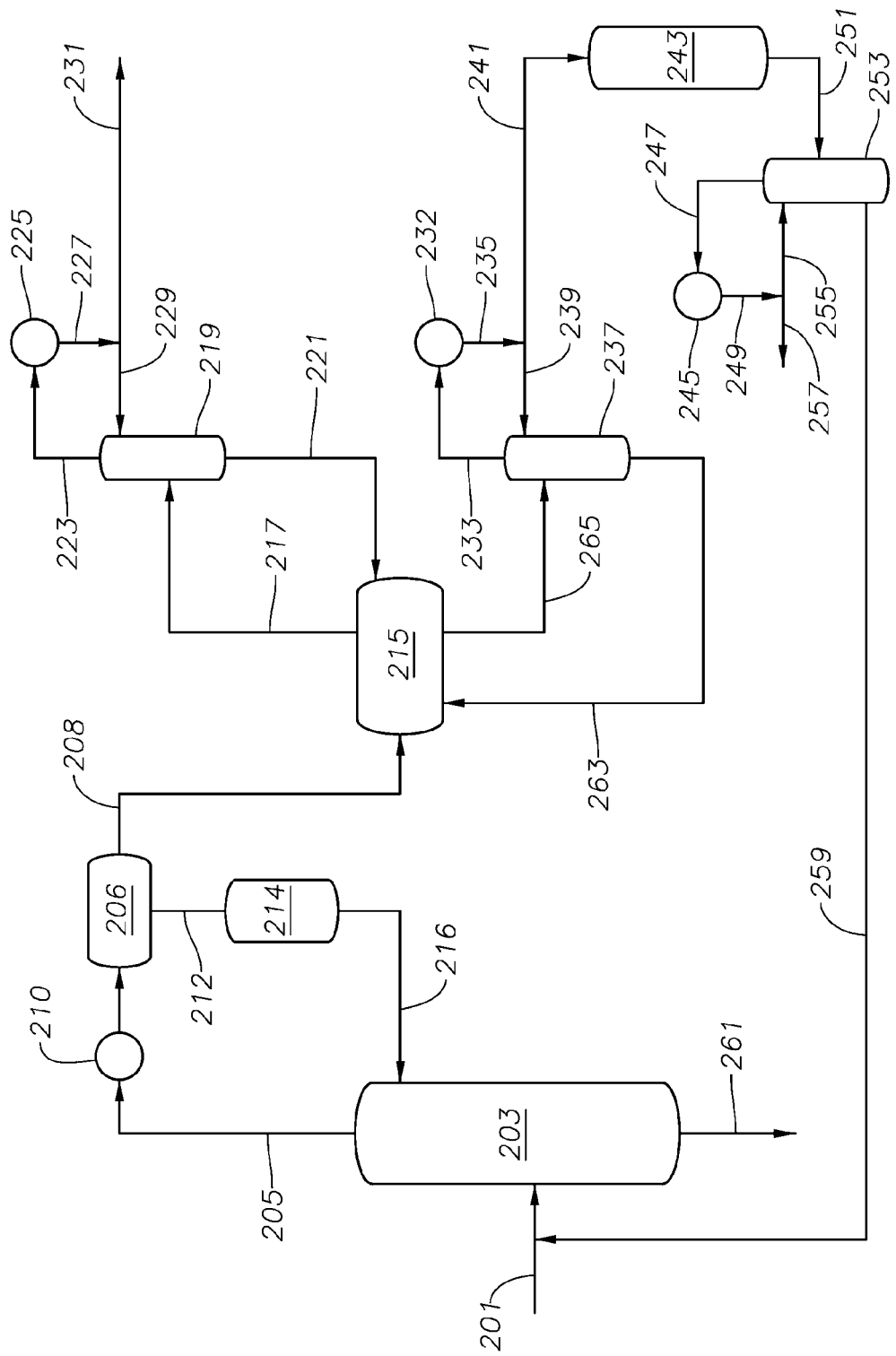

Such a configuration is shown in FIG. 3. In FIG. 3, condenser 210 provides a liquid stream from the overhead stream 205 from the xylenes re-run 203 into PX separator 206 which provides a PX-rich stream 208 and a PX-lean stream 212. As in FIGS. 1 and 2, re-run 203 is provided a feedstream 201 comprising xylenes (optionally merged with recycle from the system, e.g., a stream provided by conduit 259, as explained further herein). The liquid-phase PX separator 206 may be an adsorption unit, a membrane unit, crystallization unit, or any other technology capable of separating PX from EB, MX and OX or PX/EB from MX and OX in a liquid phase operation. In the preferred case 206 is a pressure swing adsorption unit (PSA) per se well-known in the art. The PX-rich liquid stream 208 is then fed to PX recovery unit (in a preferred embodiment a adsorptive separation unit) 215, discussed in more detail below, such as a PAREX™ unit, crystallization unit or membrane separation unit for PX recovery. The PX-lean stream 212, which contains mostly MX and OX and optionally EB, will be isomerized in the liquid phase isomerization unit 214 to raise the PX concentration. The product from the liquid isomerization is sent back to the xylenes re-run as a reflux via conduit 216.

The PX-rich stream 208 is sent to the PX recovery unit 215, which may employ crystallization technology, adsorption technology, or extraction technology, each per se well known in the art. These technologies separate PX from its isomers and are capable of producing high purity PX up to 99.9%, which is taken from unit 215 via conduit 217. Shown in FIG. 3 is the case where unit 215 is an adsorptive separation unit, such as a Parex™ Unit, in which case typically the extract 217, which comprises a desorbent, such as PDEB (paradiethylbenzene), needs to be separated, such as by distillation, from the desired extract PX in distillation column 219, which generates an overhead 223 that is condensed in condenser 225 to yield a liquid stream 227, which is a high purity PX stream. This stream 227 may be taken off via conduit 231 and optionally a portion may be returned to column 219 as reflux via conduit 229. The desorbent is returned to the PX recovery system 215 via conduit 221. Raffinate from the recovery system 215, comprising MX, OX, EB, and some PX, is removed via conduit 265 and sent to unit 237, discussed below. Again, raffinate such as in conduit 265 is often taken off (valve and/or lines not shown) and marketed as low-value solvent xylene.

All or a portion of raffinate 265, which comprises mainly MX, OX, EB, and desorbent is sent to fractionation column 237, generating overhead 233 and bottoms 263. Overhead 233 contains MX and OX, which is condensed in condenser 232 and sent via conduit 235 and then 241 to isomerization unit 243, discussed in more detail below. A portion may be returned to fractionator 237 via conduit 235 and then 239 as reflux. The desorbent in the bottoms product is returned to the unit designated 215.

A stream consisting essentially of MX and OX and EB is sent to isomerization unit 243, an apparatus per se known in the art, to isomerize the MX and OX and optionally EB to PX. Conventionally unit 243 is a vapor phase isomerization unit. Conventionally there are one or more heat exchangers or furnaces associated with the system shown in FIG. 3 between the PX recovery unit 215 and the isomerization unit that are not shown for convenience of view. Likewise, hydrogen separators and hydrogen compressors are also not shown for convenience of view. These and other features, such as valves and the like, would be apparent to one of ordinary skill in the art in possession of the present invention.

The product of the isomerization unit 243 is sent via conduit 251 to the C7-distillation tower 253, which separates the product of isomerization into a bottom stream 259 comprising equilibrium xylenes and the overhead 247, comprising C7-aromatics, e.g., benzene and toluene. The overhead product is condensed in condenser 245 and then the distribution of liquid product via conduit 249 may be apportioned as desired between conduit 257 and conduit 255, the former of which may be disposed of in numerous ways which would be well-known per se in the art, and the latter conduit returning C7-aromatics as reflux to tower 253. The bottoms product 259 of distillation tower 253 is then sent to xylenes re-run 203, either merging with feed 201 as shown in the figure, or it may be introduced by a separate inlet (not shown).

Example I

This example illustrates a near 71% energy reduction using a vapor-phase PX separator coupled with a liquid isomerization as shown in FIG. 2. Conventionally (FIG. 1), a 59 T/hr (or 519 kta) conventional PX production plant needs to vaporize and condense 2126.4 T/hr of xylenes. However, as shown in FIG. 2, the vapor-phase separator, which has the highest selectivity and 100% recovery toward PX and EB, separates the re-run overhead into a PX-rich stream containing only PX and EB and a PX-lean stream containing only MX and OX. The PX/EB is condensed (condenser not shown in figure for convenience of view) and sent to PAREX for PX recovery. The EB from PAREX is sent to a conventional isomerization unit for EB dealkylation. The MX/OX stream is condensed and isomerized back to a mixture of PX, MX and OX and is sent back to the re-run as a reflux. In this case, only 624 T/hr of xylenes needs to be vaporized and condensed, indicating a 71% reduction of energy consumption compared with FIG. 1.

Example II

This example illustrates a near 43% energy reduction using a vapor-phase PX separator with conventional selectivity and less than full recovery coupled with a liquid isomerization. As shown in FIG. 3, the PX separator 206, which has a selectivity of 6.3 and a recovery of 55% toward PX and EB, separates the re-run overhead into a PX/EB-rich stream containing more PX/EB than MX/OX and a PX-lean stream containing more MX/OX than PX/EB. The PX/EB-rich stream is sent to PAREX for PX recovery. The EB, MX and OX from the PAREX is sent to a conventional isomerization unit for EB dealkylation and MX/OX isomerization.

The PX/EB-lean stream is condensed and isomerized back to a mixture of PX, MX, OX and low level of EB and is sent back to the re-run as a reflux. FIG. 3 shows that 1206.4 T/hr of xylenes need to be vaporized and condensed, indicating a 43% reduction of energy consumption comparing to the conventional process of FIG. 1.

While the illustrative embodiments of the invention have been described with particularity, it will be understood that various other modifications will be apparent to and can be readily made by those skilled in the art without departing from the spirit and scope of the invention. However, the invention preferably is directed to the following embodiments: (I) a process for the production of paraxylene comprising: (i) providing a first feedstream, containing xylenes including paraxylene (PX) and non-xylenes, to a xylenes separator to produce a xylenes-rich second stream characterized by an increased concentration of xylenes, relative to said first feedstream, and a xylenes-lean third stream characterized by a decreased concentration of xylenes, relative to said first feedstream; (ii) passing said second stream to a first paraxylene separation step whereby paraxylene is separated from orthoxylene (OX) and metaxylene (MX) to produce a fourth stream characterized by an increased concentration of paraxylene, relative to said second stream, and a fifth stream characterized by a decreased concentration of paraxylene, relative to said second stream; (iii) passing said fourth stream to a second paraxylene separation step whereby paraxylene is separated from orthoxylene, and metaxylene, to produce a sixth stream characterized by an increased concentration of paraxylene relative to the concentration of paraxylene in said fourth stream, and a seventh stream characterized by a decreased concentration of paraxylene relative to the concentration of paraxylene in said fourth stream; (iv) passing said fifth stream to a liquid phase isomerization step whereby orthoxylene and metaxylene are isomerized to produce an eighth stream characterized by an increased concentration of paraxylene, relative to the concentration of paraxylene in said fifth stream; (v) passing at least a portion of said eighth stream to said xylenes separator (step (i)); (vi) passing said seventh stream to a vapor phase isomerization step whereby orthoxylene and metaxylene are isomerized to produce a ninth stream characterized by an increased concentration of paraxylene (and preferably a decreased concentration of ethylbenzene) relative to the concentration of paraxylene in said seventh stream; (vii) passing said ninth stream to said xylenes separator (step (i)); and also including one or more (as would be apparent to one of skill in the art in possession of the present disclosure) of the following embodiments: wherein ethylbenzene is separated with paraxylene into said fourth stream; wherein ethylbenzene is separated with metaxylene and orthoxylene into said fifth stream; wherein said first paraxylene separation step (step ii)) is selected from adsorptive separation, crystallization separation, and membrane separation; wherein said first paraxylene separation step is a vapor phase separation; wherein said first paraxylene separation step in is a liquid phase separation; wherein said liquid phase isomerization step (iv) includes a step of contacting said fifth stream with a catalyst comprising ZSM-5 characterized by one or more of the following characteristics:

the ZSM-5 is in the proton form (HZSM-5);
the ZSM-5 has a crystal size of less than 0.1 microns;
the ZSM-5 has a mesoporous surface area (MSA) greater than 45 m$^2$/g;
the ZSM-5 has a zeolite surface area (ZSA) to mesoporous surface area (MSA) ratio of less than 9;

the ZSM-5 has a silica to alumina weight ratio in the range of 20 to 50; and also (II) a process for the production of paraxylene (PX) by a xylenes loop process including the steps of: (i) separating by distillation a C8+ aromatic feed into an overhead comprising xylenes and a bottoms comprising C9+ aromatics; (ii) recovering from said overhead comprising xylenes a high purity paraxylene (PX) stream by a process selected from crystallization technology, adsorption technology, membrane technology, and extraction technology; and a paraxylene-lean stream comprising metaxylene and orthoxylene; (iii) contacting said paraxylene-lean stream with an isomerization catalyst under conditions sufficient to generate an equilibrium mixture of xylenes and passing said equilibrium mixture of xylenes to step (i); wherein the improvement comprises: (ia) separating said overhead from step (i) into a paraxylene-rich stream and a paraxylene-lean stream; (ib) passing said paraxylene-rich stream to step (ii) and contacting said paraxylene-lean stream with an isomerization catalyst under conditions sufficient to generate an equilibrium mixture of xylenes and passing said equilibrium mixture of xylenes to step (i); which may also include one or more of the following embodiments: wherein the isomerization step (iii) is under vapor phase isomerization conditions and the isomerization step (ib) is under liquid phase isomerization conditions; wherein separating step (ia) is by pressure swing adsorption and separating step (ii) is by adsorptive separation; wherein said liquid phase isomerization comprises the step of contacting the stream fed thereto, in the liquid phase, with a ZSM-5 catalyst characterized by one or more of the following characteristics:

the ZSM-5 is in the proton form (HZSM-5);

the ZSM-5 has a crystal size of less than 0.1 microns;

the ZSM-5 has a mesoporous surface area (MSA) greater than 45 m$^2$/g;

the ZSM-5 has a zeolite surface area (ZSA) to mesoporous surface area (MSA) ratio of less than 9;

the ZSM-5 has a silica to alumina weight ratio in the range of 20 to 50; and also (III) a xylene loop system comprising a distillation column fluidly connected with a paraxylene recovery unit selected from a crystallization unit and an adsorptive separation unit, fluidly connected with a first xylenes isomerization unit, the improvement comprising: inserting a subsystem between said distillation column and said paraxylene recovery unit, fluidly connected therewith, said subsystem comprising a separation unit, selected from an adsorption unit, a membrane unit, and an extraction unit, said separation unit fluidly connect with said paraxylene recovery unit and a second xylenes isomerization unit, said second xylenes isomerization unit also fluidly connected with said distillation column; which may be further modified by one or more of the following embodiments: wherein said first xylenes isomerization unit is a vapor phase xylenes isomerization unit and said second xylenes isomerization unit is a liquid phase isomerization unit; wherein said second xylenes isomerization unit comprises a ZSM-5 catalyst characterized by one or more of the following characteristics:

the ZSM-5 is in the proton form (HZSM-5);

the ZSM-5 has a crystal size of less than 0.1 microns;

the ZSM-5 has a mesoporous surface area (MSA) greater than 45 m$^2$/g;

the ZSM-5 has a zeolite surface area (ZSA) to mesoporous surface area (MSA) ratio of less than 9;

the ZSM-5 has a silica to alumina weight ratio in the range of 20 to 50.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention is and for all jurisdictions in which such incorporation is permitted. When numerical lower limits and numerical upper limits are listed herein, ranges from any lower limit to any upper limit are contemplated.

What is claimed is:

1. A xylene loop system comprising a distillation column fluidly connected with a paraxylene recovery unit selected from a crystallization unit and an adsorptive separation unit, wherein said paraxylene recovery unit is fluidly connected with a first xylenes isomerization unit, the improvement comprising:

inserting a subsystem between said distillation column and said paraxylene recovery unit, fluidly connected to said distillation column and said paraxylene recovery unit, said subsystem comprising a separation unit to effectively separate paraxylene and ethylbenzene from metaxylene and orthoxylene, selected from an adsorption unit, a membrane unit, and an extraction unit, and inserting a second xylenes isomerization unit between said subsystem and said distillation column, said second xylenes isomerization unit fluidly connected with said subsystem and said distillation column.

2. The system according to claim 1, wherein said first xylenes isomerization unit is a vapor phase xylenes isomerization unit and said second xylenes isomerization unit is a liquid phase isomerization unit.

3. The system according to claim 2, wherein said second xylenes isomerization unit comprises a ZSM-5 catalyst characterized by one or more of the following characteristics:

the ZSM-5 is in the proton form (HZSM-5);

the ZSM-5 has a crystal size of less than 0.1 microns;

the ZSM-5 has a mesoporous surface area (MSA) greater than 45 m$^2$/g;

the ZSM-5 has a zeolite surface area (ZSA) to mesoporous surface area (MSA) ratio of less than 9;

the ZSM-5 has a silica to alumina weight ratio in the range of 20 to 50.

4. The system according to claim 3, wherein said ZSM-5 catalyst is characterized by all of said characteristics.

* * * * *